United States Patent [19]

Taylor et al.

[11] Patent Number: 4,692,368

[45] Date of Patent: Sep. 8, 1987

[54] ELASTIC SPUNLACED POLYESTER-MELTBLOWN POLYETHERURETHANE LAMINATE

[75] Inventors: Jack D. Taylor, Roswell; L. Warren Collier, IV, Dunwoody, both of Ga.

[73] Assignee: Kimberly-Clark Corporation, Neenah, Wis.

[21] Appl. No.: 919,297

[22] Filed: Oct. 15, 1986

[51] Int. Cl.[4] .............................................. B32B 3/10
[52] U.S. Cl. .................................... 428/137; 156/164; 156/229; 156/240; 428/171; 428/172; 428/198; 428/284; 428/286; 428/326; 428/340; 428/296; 428/298; 428/299; 428/903; 428/910; 428/152
[58] Field of Search ............... 428/198, 137, 284, 286, 428/326, 340, 903, 910, 296, 171, 172, 298, 299, 152; 156/164, 229, 290, 324

[56] References Cited

U.S. PATENT DOCUMENTS

| | | | |
|---|---|---|---|
| 2,957,512 | 10/1960 | Wade et al. | 154/33.05 |
| 3,016,599 | 1/1962 | Perry | 28/78 |
| 3,594,266 | 7/1971 | Okazaki | 161/173 |
| 3,673,060 | 6/1972 | Murphy et al. | 161/126 |
| 3,700,545 | 10/1972 | Matsui et al. | 161/175 |
| 3,849,241 | 11/1974 | Butin et al. | 161/169 |
| 3,932,682 | 1/1976 | Loft et al. | 428/296 |
| 3,949,128 | 4/1976 | Ostermeier | 428/152 |
| 4,100,324 | 7/1978 | Anderson et al. | 428/288 |
| 4,107,364 | 8/1978 | Sisson | 428/296 |
| 4,209,563 | 6/1980 | Sisson | 428/296 |
| 4,223,101 | 9/1980 | Fine et al. | 528/76 |
| 4,234,652 | 11/1980 | Vanomi et al. | 428/296 |
| 4,251,587 | 2/1981 | Mimura et al. | 428/233 |
| 4,275,105 | 6/1981 | Boyd et al. | 428/298 |
| 4,296,163 | 10/1981 | Emi et al. | 428/212 |
| 4,318,408 | 3/1982 | Korpman | 128/287 |
| 4,375,446 | 3/1983 | Fujii | 264/518 |
| 4,426,417 | 1/1984 | Meitner et al. | 428/195 |
| 4,426,420 | 1/1984 | Likhyani | 428/224 |
| 4,429,002 | 1/1984 | Fukada et al. | 428/296 |
| 4,438,172 | 3/1984 | Katsutoshi et al. | 428/298 |
| 4,442,062 | 4/1984 | Fujii | 264/518 |
| 4,443,511 | 4/1984 | Worden et al. | 428/910 |
| 4,555,811 | 12/1985 | Shimalla | 2/51 |
| 4,588,630 | 5/1986 | Shimalla | 428/910 |
| 4,623,576 | 11/1986 | Lloyd et al. | 428/903 |

FOREIGN PATENT DOCUMENTS 1575830 10/1980 United Kingdom.
2132939A 7/1984 United Kingdom.

OTHER PUBLICATIONS

Du Pont's, "A Reference Guide-Sontara".
Du Pont's Material Safety Data Sheet.
K. J. Quinn & Co., Inc.'s Technical Bulletin, Q-Thane Thermoplastic Elastomers, PE 90-100.

Primary Examiner—James J. Bell
Attorney, Agent, or Firm—Joseph P. Harps

[57] ABSTRACT

A laminate which is elastic in at least one direction, includes an elastic sheet having at least one nonelastic nonwoven web joined thereto at least at two areas. The nonelastic web is gathered between the two areas. The sheet is formed from an aromatic polyetherurethane and the nonelastic nonwoven web includes spunlaced hydraulically entangled polyester fibers. The nonelastic nonwoven web may also include rayon or wood pulp fibers.

22 Claims, 7 Drawing Figures

ELASTIC SPUNLACED POLYESTER-MELTBLOWN POLYETHERURETHANE LAMINATE

FIELD OF THE INVENTION

The present invention falls within the field of elastic fabrics, for example, disposable elastic fabrics which may be utilized in the manufacture of wearing apparel and other items which conform about another item.

BACKGROUND OF THE INVENTION

The advent of formation of plastic materials such as plastic sheets, films and nonwoven webs by extrusion processes such as, for example, slot film extrusion, blown bubble film extrusion, meltblowing of nonwoven webs and spinbonding of nonwoven webs allowed a wide variety of products to be manufactured so inexpensively that they could be viewed as disposable after only one or a few uses. Representatives of such products include diapers, tissues, wipes and mattress pads.

Some of the problems in this area are the provision of a bulky elastic material which is resilient and flexible while still having a pleasing feel. A particular problem which has confronted those in the art is the provision of a bulky elastic material which does not feel plastic or rubbery. Other characteristics which are desirable are the ability to withstand unraveling during cutting and sewing operations, good puncture resistance, wet strength and a low linting factor.

DEFINITIONS

The term "elastic" is used herein to mean any material which, upon application of a biasing force, is stretchable, that is, elongatable, to a stretched, biased length which is at least about 125 percent, that is about one and one quarter, of its relaxed, unbiased length, and which, will recover at least 40 percent of its elongation upon release of the stretching, elongating force. A hypothetical example which would satisfy this definition of an elastic material would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length, for example, 100 percent or more, and many of these will recover to substantially their original relaxed length, for example, to within 105 percent of their original relaxed length, upon release of the stretching, elongating force.

As used herein, the term "nonelastic" refers to any material which does not fall within the definition of "elastic," above.

As used herein the term "recover" refers to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would be elongated 50 percent and would have a stretched length that is 150 percent of its relaxed length. If this exemplary stretched material contracted, that is recovered to a length of one and one tenth (1.1) inches after release of the biasing and stretching force, the material would have recovered 80 percent (0.5 inch) of its elongation.

As used herein the term "nonwoven web" means a web of material which has been formed without use of weaving processes which produce a structure of individual fibers or threads which are interwoven in an identifiable repeating manner. Nonwoven webs have been, in the past, formed by a variety of processes such as, for example, meltblowing processes, spinbonding processes, film aperturing processes and staple fiber carding processes.

As used herein the term "microfibers" means small diameter fibers having an average diameter not greater than about 100 microns, preferably having a diameter of from about 0.5 microns to about 50 microns, more preferably having an average diameter of from about 4 microns to about 40 microns.

As used herein the term "meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter. Thereafter, the meltblown microfibers are carried by the high velocity gas stream and are deposited on a collecting surface to form a web of randomly disbursed meltblown microfibers. Such a process is disclosed, for example, in U.S. Pat. No. 3,849,241 to Butin and the disclosure of this patent is hereby incorporated by reference.

As used herein the term "sheet" means a layer which may be either a film or a nonwoven web.

As used herein, the term "stretch-bonded laminate" refers to a material having at least two layers of nonwoven webs and/or films with at least one of the layers of nonwoven webs and/or films being elastic and at least one of the layers of the nonwoven webs and/or films being nonelastic. The elastic nonwoven web or film layer is joined to the nonelastic nonwoven web or film layer at intermittent joining points or areas while the nonwoven webs and/or films are in juxtaposed configuration and while the elastic nonwoven web or film has a tensioning force applied thereto in order to bring the elastic nonwoven web or film to a stretched condition. Upon removal of the tensioning force after joining of the webs and/or films, the elastic nonwoven web or film will attempt to recover to its unstretched condition and will thereby gather the nonelastic nonwoven web or film between the points or areas of joining of the two layers. The composite material is elastic in the direction of stretching of the elastic layer during joining of the layers and may be stretched until the gathers of the nonelastic nonwoven web or film layer have been removed. A stretch-bonded laminate may include more than two layers. For example, the elastic nonwoven web or film may have a nonelastic nonwoven web or film joined to both of its sides while it is in a stretched condition so that a three layer nonwoven web or film composite is formed having the structure of—gathered nonelastic (nonwoven web or film)/elastic (nonwoven web or film)/gathered nonelastic (nonwoven web or film). Yet other combinations of elastic and nonelastic layers may be utilized.

As used herein the term "palindromic" means a multi-layer laminate, for example a stretch-bonded laminate, which is substantially symmetrical. Examples of palindromic laminates would have layer configurations of A/B/A, A/B/B/A, A/A/B/B/A/A, A/B/C/B/A, etc. Examples of non-palindromic layer configurations would include A/B/C, A/B/C/A, A/B/C/D, etc.

As used herein the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solid solvents, particulates and materials added to enhance processability of the composition.

OBJECTS OF THE INVENTION

Accordingly, it is an object of the present invention to provide an elastic laminate which is elastic, bulky and has a feel suitable for use in a variety of applications.

Another object of the present invention is to provide an elastic stretch-bonded laminate which is elastic, bulky and has a feel suitable for use in a variety of applications.

Yet another object of the present invention is to provide a bulky laminate including a layer of meltblown polyetherurethane fibers joined to at least one layer of spunlaced hydraulically entangled polyester fibers.

An even further object of the present invention is to provide a bulky stretch-bonded laminate including a layer of meltblown polyetherurethane fibers joined to at least one layer of spunlaced hydraulically entangled polyester fibers.

Still further objects and the broad scope of applicability of the present invention will become apparent to those of skill in the art from the details given hereinafter. However, it should be understood that the detailed description of the presently preferred embodiment of the present invention is given herein only by way of illustration because various changes and modifications well within the spirit and scope of the invention will become apparent to those of skill in the art in view of this detailed description.

SUMMARY OF THE INVENTION

The present invention provides an elastic laminate which is elastic in at least one direction and which includes an elastic sheet and at least one nonelastic, nonwoven web joined to the elastic sheet at least at two areas, with the nonelastic web being gathered between the two areas.

The elastic sheet is formed from an aromatic polyetherurethane having a melt flow of from about 30 grams per ten minutes to about 60 grams per ten minutes when measured at 190 degrees C. and with a 8,700 gram load; an elongation of from about 400 percent to about 600 percent; a modulus of elongation at 100 percent of from about 800 psi to about 1,000 psi; a modulus of elongation at 300 percent of from about 1,600 psi to about 1,800 psi; a specific gravity of from about 1.10 to about 1.3 and an abrasion resistance of from about 20 mg to about 30 mg per 1,000 cycles. The aromatic polyetherurethane has a melt index of from about 5 grams per ten minutes to about 20 grams per ten minutes when measured at 190 degrees C. under a 2,160 gram load. More particularly, the polyetherurethane has a melt index of about 13.8 grams per ten minutes when measured at 190 degrees C. and under a 2,160 gram load; an elongation of about 500 percent; a modulus of elongation at 100 percent of about 900 psi; a modulus of elongation at 300 percent of about 1,700 psi; a specific gravity of about 1.20; and an abrasion resistance of about 25 mg per 1,000 cycles. The elastic sheet is preferably an elastic nonwoven web of meltblown fibers, for example meltblown microfibers. The basis weight of the elastic nonwoven web of meltblown fibers in the relaxed condition may vary from about 10 grams per square meter to about 200 grams per square meter. For example, the basis weight if the elastic nonwoven web may vary from about 20 grams per square meter to about 100 grams per square meter.

The nonelastic web is a nonwoven web of spunlaced hydraulically entangled polyester fibers. The nonelastic web may also include rayon fibers or wood pulp fibers. The nonelastic web has a machine direction sheet grab tensile of from about 10 pounds to about 75 pounds; a cross-machine direction sheet grab tensile of from about 5 pounds to about 50 pounds; a machine direction trapezoid tear of from about 3 pounds to about 40 pounds; a cross-machine direction trapezoid tear of from about 2 pounds to about 45 pounds; a thickness of from about 10 mils to about 45 mils and a basis weight of from about 1 ounce to about 5 ounces per square yard. The nonelastic web may be apertured.

One particular nonelastic web of spunlaced hydraulically entangled polyester fibers has a basis weight of 1.0 ounces per square yard; a thickness of about 11 mils; a machine direction sheet grab tensile of about 17 pounds; a cross machine direction sheet grab tensile of about 8 pounds; a machine direction trapezoid tear of about 7 pounds and a cross machine direction trapezoid tear of about 3 pounds.

One particular apertured nonelastic web of spunlaced hydraulically entangled polyester fibers has a basis weight of about 1.3 ounces per square yard; a thickness of about 18 mils; a machine direction sheet grab tensile of about 25 pounds; a cross-machine direction sheet grab tensile of about 14 pounds; a machine direction trapezoid tear of about 7 pounds and a cross machine direction trapezoid tear of about 5 pounds.

In one embodiment the laminate is a stretch-bonded laminate which is elastic in at least one direction and which is adapted to stretch from at least about 50 percent to about 100 percent, for example, 75 percent, in that direction. This laminate includes an inner elastic nonwoven web of meltblown polyetherurethane fibers having a relaxed basis weight of from about 50 grams per square meter to about 100 grams per square meter. Also included in this laminate are two outer nonelastic webs of hydraulically entangled spunlaced polyester fibers, each having an ungathered basis weight of from about 0.9 to about 1.1 ounches per square yard; a thickness of from about 10 mils to about 12 mils; a machine direction sheet grab tensile of from about 16 pounds to 18 pounds; a cross-machine direction sheet grab tensile of from about 7 pounds to about 9 pounds; a machine direction trapezoid tear of from about 6 pounds to about 8 pounds and a cross-machine direction trapezoid tear of from about 2 pounds to about 4 pounds.

Alternatively, one of the nonelastic webs of hydraulically entangled spunlaced polyester fibers could be deleted with a nonelastic web of dry laid polyester staple fibers joined by a hot melt polyester-based, powder-form adhesive being substituted therefor. The web of dry laid polyester-based staple fiber may have a basis weight of from about 5 grams per square meter to about 50 grams per square meter, for example about 14 grams per square meter. The polyester staple fibers have a length of from about 1.0 inches to about 2.0 inches, for example about 1.5 inches; a denier of from about 1.0 to about 2.0, for example a denier of about 1.5; a melting point of from about 450 degrees F. to about 500 degrees F., for example about 482 degrees F. and an elongation to break of from about 30 percent to about 50 percent, for example about 40 percent. The hot melt polyester-based adhesive used to hold the polyester staple fibers in a self-supporting web configuration has a density of from about 1.20 g/cm$^3$ to about 1.30 g/cm$^3$, for example about 1.24 g/cm$^3$ and a melt viscosity of from about 2,000 to 2,200 poise at 190 degrees C., for example a melt viscosity of about 2,100 poise at 190 degrees C. The dry laid web includes from about 78 percent to about 82 percent, by weight, of the polyester staple fibers and from about 18 percent to about 22 percent, by weight, of the hot melt adhesive.

DETAILED DESCRIPTION OF THE INVENTION

Figure 1:
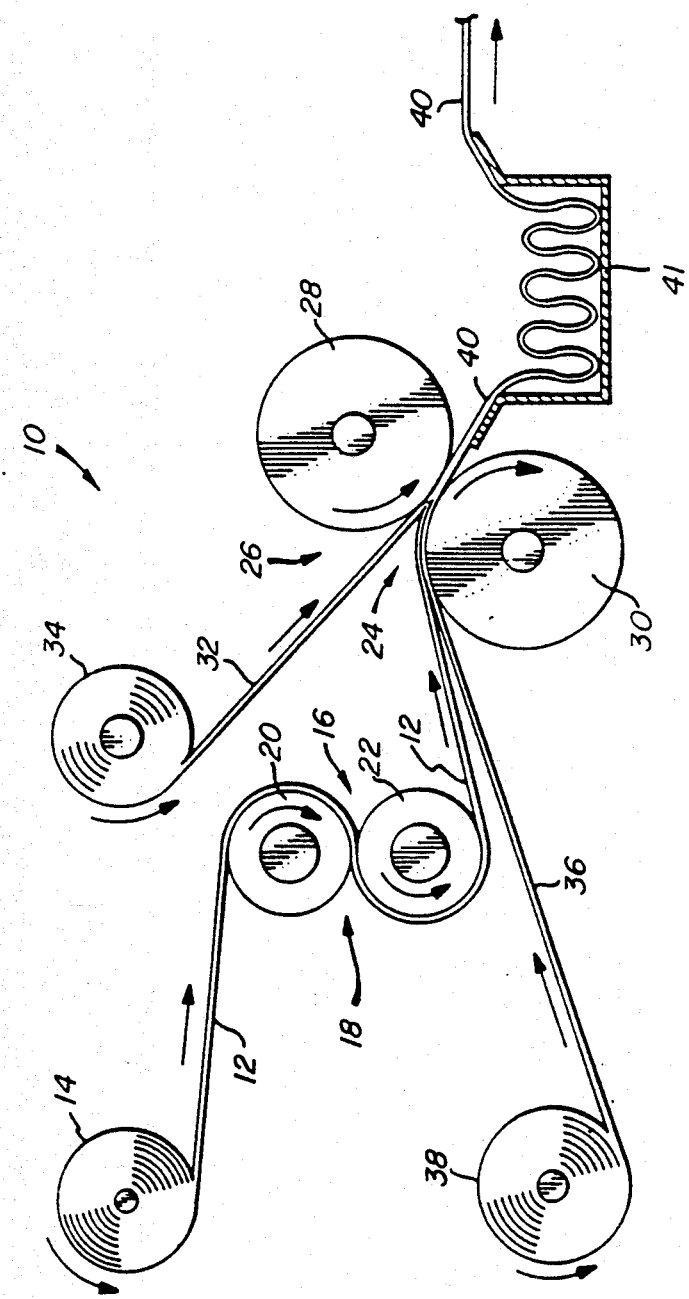
FIG. 1 is a schematic representation of a process for forming a stretch-bonded laminate in accordance with the present invention.

Referring now to the drawings where like reference numbers represent like or equivalent structure and, in particular, to FIG. 1, there is schematically illustrated at 10 a process for forming a stretch-bonded laminate by heat-bonding a nonelastic web to each of the two opposite sides of an elastic sheet which may be an elastic film or an elastic nonwoven web. The elastic sheet 12 is formed from an aromatic polyetherurethane having a melt flow of from about 30 grams per ten minutes to about 60 grams per ten minutes when measured at 190 degrees C. and under a 8,700 gram load; an elongation of from about 400 percent to about 600 percent; a modulus of elongation at 100 percent of from about 800 to about 1,000 psi; a modulus of elongation at 300 percent of from about 1,600 to about 1,800 psi; a specific gravity of from about 1.1 to about 1.3 and an abrasion resistance of from about 20–30 mg per 1,000 cycles. The aromatic polyetherurethane may have a melt index of from about 5 grams per 10 minutes to about 20 grams per 10 minutes when measured at 190 degrees C. under a 2,160 gram load. More particularly, the aromatic polyetherurethane has a melt flow of about 13.8 grams per ten minutes when measured at 190 degrees C. under a 2,160 gram load; an elongation of about 500 percent; a modulus of elongation at 100 percent of about 900 psi; a modulus of elongation at 300 percent of about 1,700 psi; a specific gravity of about 1.20 and an abrasion resistance of about 25 mg per 1,000 cycles. Preferably, the elastic sheet 12 is a web of meltblown polyetherurethane fibers, for example microfibers, having a basis weight of from about 10 grams per square meter to about 200 grams per square meter. For example, the web may have a basis weight of from about 20 grams per square meter to about 100 grams per square meter.

The elastic sheet 12 may be unwound from a supply roll 14 of the elastic sheet material. The sheet 12 then travels in the direction indicated by the arrows associated therewith and passes through the nip 16 of the S roll arrangement 18 formed by the stacked rollers 20 and 22. Alternatively, the sheet 12 may be formed by known extrusion processes, for example, known film formation or known meltblowing processes, and passed directly through the nip 16 without being first stored on the supply roll 14. The sheet 12 passes through the nip 16 in a reverse-S path as indicated by the rotation direction arrows associated with the stacked rollers 20 and 22. From the S roll arrangement 18 the sheet 12 passes through the pressure nip 24 formed by a bonder roller arrangement 26. The bonder roller arrangement 26 includes a patterned calender embossing roller 28, for example a thermal pin embossing roller, and a smooth anvil roller 30.

A first nonelastic web 32 is unwound from a supply roll 34 and a second nonelastic web 36 is unrolled from a supply roll 38. The nonelastic nonwoven webs 32 and 36 are preferably formed from spunlaced web of hydraulically entangled polyester fibers. One or both of the webs 32 and 36 may also include rayon fibers or wood pulp fibers. The webs 32 and 36 each have a machine direction sheet grab tensile of from about 10 pounds to about 75 pounds; a cross-machine direction sheet grab tensile of from about 5 pounds to 50 pounds; a machine direction trapezoid tear of from about 3 pounds to about 40 pounds; a cross-machine trapezoid tear of from about 2 pounds to about 45 pounds; a thickness of from about 10 mils to about 45 mils and a basis weight of from about 1 to 5 ounces per square yard. One or both of the webs 32 and 36 may be apertured.

One particular nonelastic web has a basis weight of about 1.0 ounches per square yard; a thickness of about 11 mils; a machine direction sheet grab tensile of about 17 pounds; a cross machine direction sheet grab tensile of about 8 pounds; a machine direction trapezoid tear of about 7 pounds and a cross machine direction trapezoid tear of about 3 pounds.

One particular apertured nonelastic web has a basis weight of about 1.3 ounces per square yard; a thickness of about 18 mils; a machine grab tensile of about 25 pounds; a cross-machine grab tensile of about 14 pounds; a machine direction trapezoid tear of about 7 pounds and a cross machine direction trapezoid tear of about 5 pounds.

Nonelastic webs of hydraulically entangled fibers of this type can be obtained from Du Pont under the trade designation Sontara, for example, Sontara 8001 and Sontara 8010. Typical physical characteristics of Sontara materials, as evidenced by Du Pont literature are stated below in Table I.

TABLE I

| TYPE | UNIT WEIGHT (oz/yd.$^2$) | THICKNESS (mils) | SHEET GRAB TENSILE (lbs) MD | SHEET GRAB TENSILE (lbs) XD | TRAPEZOID TEAR (lbs) MD | TRAPEZOID TEAR (lbs) XD | MULLEN BURST (psi) | FRAZIER AIR PERMEABILITY (CFM/ft$^2$ @ 0.5" H$_2$O) |
|---|---|---|---|---|---|---|---|---|
| 100% Polyester | | | | | | | | |
| 8000 | 1.2 | 14 | 23 | 14 | 6 | 5 | 40 | 500 |
| 8001 | 1.0 | 11 | 17 | 8 | 7 | 3 | 23 | 600 |
| 8010** | 1.3 | 18 | 25 | 14 | 7 | 5 | 33 | 750 |
| 8100 | 4.0 | 40 | 70 | 45 | 35 | 40 | 120 | 215 |
| 8103 | 2.0 | 22 | 40 | 22 | 14 | 8 | 50 | 290 |
| 8122** | 2.4 | 27 | 45 | 25 | 15 | 7 | 57 | 320 |
| 8125** | 1.8 | 17 | 31 | 16 | 11 | 5 | 44 | 420 |
| 70/30 Rayon/Polyester Blend | | | | | | | | |
| 8407** | 1.5 | 16 | 11 | 8 | 5 | 7 | 20 | 780 |
| 8423 | 2.3 | 26 | 13 | 15 | 4 | 5 | 24 | 255 |
| 55/45 Woodpulp/Polyester Blend | | | | | | | | |
| 8801 | 2.0 | 14 | 35 | 17 | 8 | 6 | 35 | 85 |
| 8808 | 2.0 | 14 | 35 | 17 | 8 | 6 | 35 | 85 |
| ASTM Test Method | D1117 Sec. 17 | D1117 Sec. 19 | D1117 Sec. 7 | | D1117 Sec. 14 | | D1117 Sec. 8 | D1117 Sec. 6 |

**Apertured style

Alternatively, one of the nonelastic webs of hydraulically entangled spunlaced polyester fibers could be deleted with a nonelastic web of dry laid polyester staple fibers joined by a hot melt polyester-based, powder-form adhesive being substituted therefor. The dry laid web is formed by dry laying the polyester staple fibers, adding the polyester-based adhesive in a ground form from above and applying heat to melt the adhesive and join the polyester staple fibers. The web of dry laid polyester-based staple fiber may have a basis weight of from about 5 grams per square meter to about 50 grams per square meter, for example about 14 grams per square meter. The polyester staple fibers have a length of from about 1.0 inches to about 2.0 inches, for example about 1.5 inches; a denier of from about 1.0 to about 2.0, for example a denier of about 1.5; a melting point of from about 450 degrees F. to about 500 degrees F., for example about 482 degrees F. and an elongation to break of from about 30 percent to about 50 percent, for example about 40 percent. The hot melt polyester-based adhesive has a density of from about 1.20 g/cm$^3$ to about 1.30 g/cm$^3$, for example about 1.24 g/cm$^3$ and a melt viscosity of from about 2,000 to 2,200 poise at 190 degrees C., for example a melt viscosity of about 2,100 poise at 190 degrees C. The dry laid web includes from about 78 percent to about 82 percent, by weight, of the polyester staple fibers and from about 18 percent to about 22 percent, by weight, of the hot melt adhesive.

One such dry laid web may be obtained from the Carolina Formed Fabrics Corporation of Greenville, S.C. under the trade designation Carelle. Carelle comes in a variety of basis weights and includes from about 78 percent to about 82 percent, by weight, of Kodel 41D polyester staple fibers and from about 18 percent to about 22 percent, by weight, of a polyester-based hot melt adhesive which may be obtained from Eastman under the trade designation FA-300.

The first nonelastic web 32 and the second nonelastic web 36 travel in the directions indicated by the arrows associated respectively therewith as supply rolls 34 and 38 rotate in the directions indicated by the respective arrows associated therewith. Both of the nonelastic webs 32 and 36 are directed to pass through the pressure nip 24 of the bonder roller arrangement 26 on the two opposite sides of the elastic sheet 12 as illustrated in FIG. 1. By virtue of the fact that the peripheral linear speed of the rollers 20 and 22 of the S roll arrangement 18 is controlled to be less than the peripheral linear speed of the rollers 28 and 30 of the bonder roll arrangement 26, the sheet 12 is stretched to a selected percent elongation and maintained in such stretched condition during bonding of the nonelastic webs 32 and 36 to the sheet 12 during their passage through the bonder roller arrangement 26. The degree of stretching of the elastic sheet 12 between the S roller arrangement 18 and the bonder roller arrangement 26 may be varied within the elastic limits of the polyetherurethane sheet 12 to effect different degrees of elongation (elasticity) of the stretch-bonded laminate formed upon bonding of the nonelastic webs 32 and 36 to the elastic sheet 12. In practice it has been found that an elastic stretch-bonded laminate having the ability to stretch at least 50 percent is desirable. For example, an elastic stretch-bonded laminate which is able to stretch from about 50 percent to about 100 percent is desirable. More particularly, an elastic stretch-bonded laminate which is able to stretch about 75 percent is more desirable. In order to form a stretch-bonded laminate having the above degrees of elasticity, it is necessary for the elastic sheet 12 to be stretched to a significantly greater degree upon bonding of the nonelastic webs 32 and 36 thereto. In this regard it has been generally found that the elastic sheet 12 should, upon bonding of the nonelastic webs 32 and 36 thereto, be stretched approximately two times the degree of desired elasticity in the stretch-bonded laminate. Thus, if a stretch-bonded laminate having 100 percent elasticity is desired, the elastic sheet 12 should be stretched about 200 percent at the moment of bonding.

While many bonding methods may be possible, a preferred method of bonding is by thermal bonding and, in particular, by thermal pin embossment where one or both of the patterned embossing calender roller 28 and the smooth anvil roller 30 are heated and the pressure between these two rollers is adjusted by well-known means to provide the desired temperature and bonding pressure to bond the webs 32 and 36 to the sheet 12 and thereby form a composite stretch-bonded elastic laminate 40. In thermal pin embossment bonding, the webs 32 and 36 are bound to the elastic sheet 12 by the action of lands or pins (not shown) which protrude from the calender roller 28 and cooperate with the anvil roller 30 to apply heat and pressure to selected intermittent areas of the three materials 12, 32 and 36 as they pass through the nip 24. This serves to bond them together. A variety of different bonding patterns can be effected in this manner to create a number of different visual effects. Representative bonding patterns are illustrated in FIGS. 3 through 7.

The elastic sheet 12 of the composite elastic laminate 40, upon emergence of the composite elastic laminate 40 from the pressure nip 24 of the bonder roll arrangement 26, is immediately relaxed and quickly recovers and gathers the nonelastic webs 32 and 36 between the intermittent bond areas formed by the bonder roller arrangement 26. Because the direction of stretching of the elastic sheet 12 is generally the same as the direction of travel of the three materials 12, 32 and 36 the generally parallel gathers in the nonelastic webs 32 and 36 will be generally perpendicular to the direction of travel of the composite elastic laminate 40. Thereafter the composite elastic laminate 40 passes to a holding box 41 where it is maintained in a relaxed, unstretched condition for a length of time for the elastic sheet 12 to cool sufficiently to avoid its cooling while it is in a stretched condition and thereby losing all or a considerable proportion of its ability to contract from the stretched dimensions which it had assumed during bonding.

If the composite elastic laminate 40 is to be dyed, the holding box 41 may also serve as an arrangement to apply a liquid dye to the composite elastic laminate 40.

After a brief untensioned period of, for example, up to about 30 seconds, e.g., from about 3 seconds to about 20 seconds, in the holding box 41, the composite elastic laminate 40 is withdrawn therefrom and transferred to a storage roll (not shown). The provision of the holding box 41 or an equivalent structure allows the untensioned heat-bonded composite elastic laminate 40 to stabilize, that is cool, while it is in an untensioned arrangement. This allows the elastic sheet 12 to contract and gather the gatherable web immediately after bonding of the webs to each other. Additionally, this allows the elastic sheet 12 to cool in a relaxed, that is nontensioned, condition which avoids the elastic web becoming set at the stretched dimensions which it had assumed during bonding. If the elastic sheet 12 were to set in the tensioned state it would be unable to contract and form the generally parallel gathers in the nonelastic webs 32 and 36. Accordingly, the composite material 40 would not possess elasticity because any significant stretching of the composite would result in tearing of the nonelastic webs 32 and 36. In order to avoid loss of part or all of the elasticity of the composite elastic laminate 40, the composite elastic laminate 40 should be transferred to the storage roll in only a slightly tensioned condition. Also, the composite elastic laminate 40 should be stored under only slight tension.

The stretch-bonded laminate can be provided with two directional stretch by stretching the sheet 12 in both the machine direction and cross machine direction at the moment of bonding of the webs 32 and 36 to the sheet 12. Conventional apparatus for effecting such two direction stretching includes tenter frame arrangements or the use of arched roller systems as is known in the art.

Figure 2:
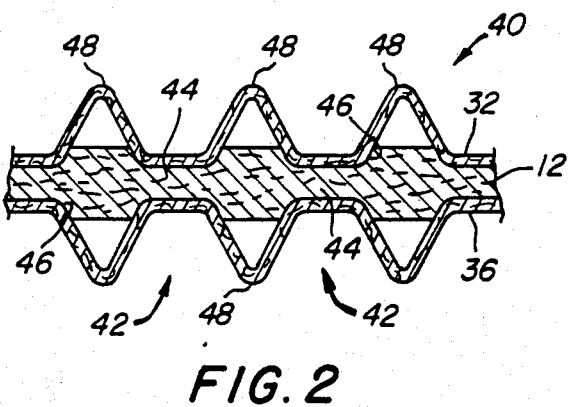
FIG. 2 is a cross-section of a stretch-bonded laminate formed by the process illustrated in FIG. 1 with the laminate being in a relaxed condition to illustrate the gathers.
Figure 3:
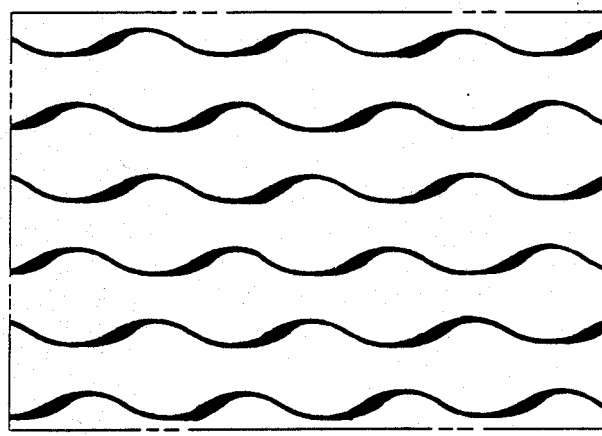
FIG. 3 is a plan view of a stretch-bonded laminate illustrating a bonding pattern.
Figure 4:
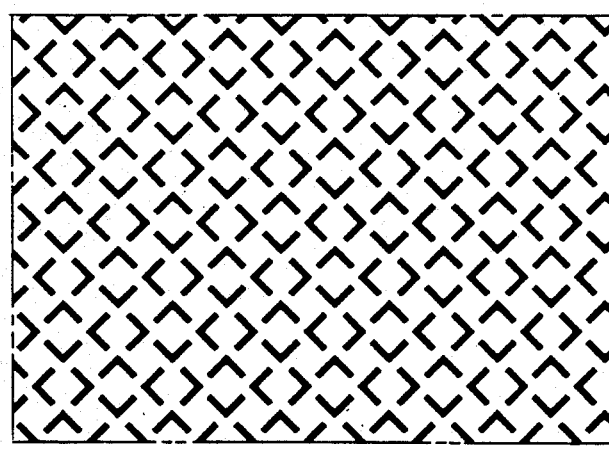
FIG. 4 is a plan view of a stretch-bonded laminate illustrating another bonding pattern.
Figure 5:
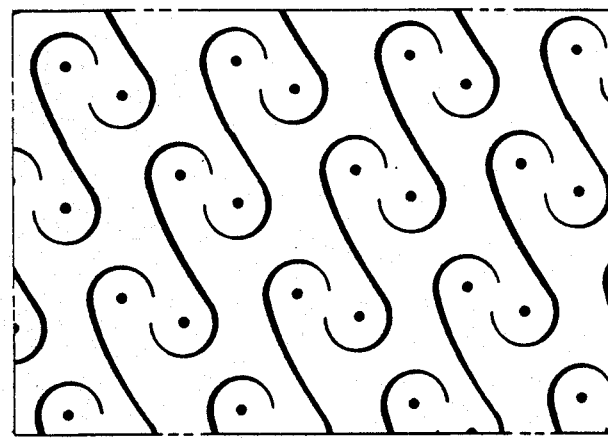
FIG. 5 is a plan view of a stretch-bonded laminate illustrating yet another bonding pattern.
Figure 6:
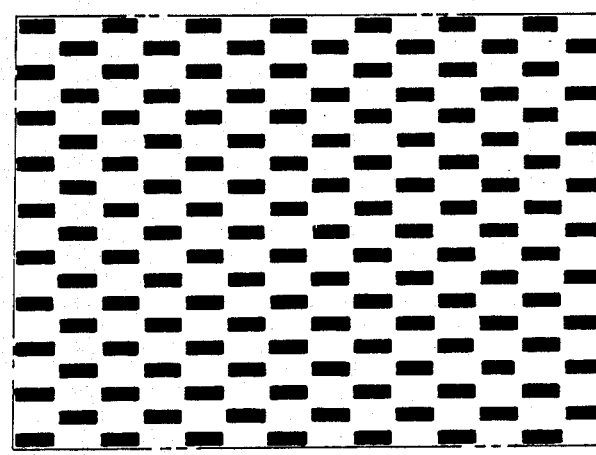
FIG. 6 is a plan view of a stretch-bonded laminate illustrating one other bonding pattern.

FIG. 2 which is a cross-sectional view of the elastic composite laminate 40 illustrates that the elastic composite laminate 40 has a plurality of embossed bond sites 42 formed by the action of the raised portions of the embossing calender roller 28 in cooperation with the anvil roller 30. The temperature and pressure maintained in the nip 24 between the calender roller 28 and the anvil roller 30 was such that the pressure and temperature imposed by the raised portions of the calender roller 28 formed indentations 44 within the elastic sheet 12 by softening or melting the portions of the sheet 12. The peripheral portions 46 of the indentations 44 of the sheet 12 include a resolidified portion of the material which was formerly located in the indented area 44. The peripheral portions 46, upon resolidification after their softening or melting in the pressure nip 24 of calender roller 28 and anvil roller 30, tend to form a reasonably strong bond with the overlaid nonelastic webs 32 and 36. The nonelastic webs 32 and 36 are gathered between the bond sites 42 and these gathers are illustrated at 48.

The elastic laminates of the present invention which have outer hydraulically entangled spunlaced nonwoven webs possess a number of desirable characteristics such as, for example, nonraveling during cut and sew operations, good puncture resistance, good wet strength and low linting. The material is drapeable and has a soft feel as a result of the outer hydraulically entangled surface webs.

EXAMPLES 1–8

Figure 7:
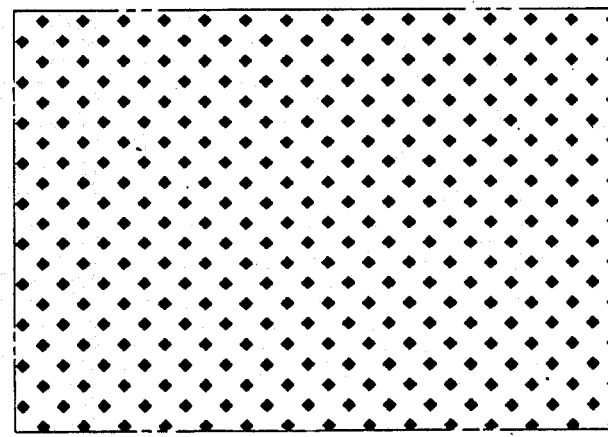
FIG. 7 is a plan view of a stretch-bonded laminate illustrating a further bonding pattern.

The elastic laminates of Examples 1–8 were made in accordance with the present invention by stretch-bonding two hydraulically entangled nonwoven webs of Sontara obtained from DuPont and selected from those listed in Table I to the opposite sides of a web of meltblown fibers formed from a polyetherurethane obtained from K. J. Quinn under the trade designation Q-thane PE90. The bonding pattern used is shown in FIG. 7. The Sontara on the calender side of the elastic meltblown is given in the column entitled "Sontara Calender Side" of Table II. The Sontara on the anvil side of the elastic meltblown is given in the column entitled "Sontara Anvil Side". The basis weight in grams per square meter of the Q-thane PE90 meltblown fibers web is given in the column entitled "Basis Weight PE90 Web". The temperature in degrees F. of the calender roll is given in the column entitled "Calender Temperature," and the temperature in degrees F. of the anvil roll is given in the column entitled "Anvil Temperature". At the moment of bonding, the web of meltblown PE90 fibers was stretched approximately the percent given in the column entitled "Percent Stretch at Bonding". The percent stretch in the final elastic laminate, when the gathered layers are fully extended, is given in the column "Percent Stretch in Laminate".

TABLE II

| Example | Sontara Calender Side | Sontara Anvil Side | Basis Weight PE90 Web (gm/m$^2$) | Calender Temperature (°F.) | Anvil Temperature (°F.) | Percent Stretch at Bonding | Percent Stretch in Laminate |
|---|---|---|---|---|---|---|---|
| 1 | 8001 | 8010 | 60 | 232 | 228–229 | 175 | 90 |
| 2 | 8407 | 8407 | 80 | 236 | 239 | 175 | 100 |
| 3 | 8407 | 8407 | 80 | 226 | 225 | 175 | 120 |
| 4 | 8407 | 8407 | 60 | 223 | 216 | 175 | 90 |
| 5 | 8407 | 8001 | 60 | 227 | 225 | 175 | 70 |

TABLE II-continued

| Example | Sontara Calender Side | Sontara Anvil Side | Basis Weight PE90 Web (gm/m²) | Calender Temperature (°F.) | Anvil Temperature (°F.) | Percent Stretch at Bonding | Percent Stretch in Laminate |
|---|---|---|---|---|---|---|---|
| 6 | 8407 | 8001 | 60 | 227 | 225 | 238 | 65 |
| 7 | 8407 | 8001 | 60 | 207 | 203 | 175 | 80 |
| 8 | 8407 | 8001 | 80 | 209 | 203 | 175 | 140 |

Comments
Example 1 The uniformity of the stretch-bonded laminate is very good. Bonding of the Sontara 8001 is excellent. Bonding of the Sontara 8010 is good.
Example 2 Bonding is very good. The stretch-bonded laminate looks like a crocheted fabric.
Example 3 Bonding is good, but not quite as good as Example 2.
Example 4 Bonding is good.
Example 5 Bonding is very good.
Example 6 Bonding is good.
Example 8 Bonding is better on the calender side than it is on the anvil side. The bonding on both sides can be improved.

It is to be understood that the above disclosure of the presently preferred embodiment of the invention is to be taken as illustrative of the invention. Further, it is clear that, in view of the present disclosure, those of skill in the art should be capable of making numerous modifications without departing from the true spirit and scope of the invention. For example, different combinations of nonelastic webs and elastic sheets could be stretch-bonded together. In particular, the elastic laminate of the present invention would include only two layers of material with one of the layers being the elastic sheet of polyetherurethane material and the other layer being a nonelastic layer of spunlaced polyester.

What is claimed is:

1. A laminate which is elastic in at least one direction, said laminate comprising:
   an elastic sheet comprising a polyetherurethane material;
   at least one nonelastic nonwoven web of spunlaced hydraulically entangled polyester fibers joined to said elastic sheet at least at two areas, said nonelastic web being gathered between said two areas.

2. The laminate of claim 1, wherein said elastic sheet is an elastic nonwoven web of meltblown fibers.

3. The laminate of claim 2, wherein the relaxed basis weight of the elastic nonwoven web is from about 10 grams per square meter to about 200 grams per square meter.

4. The laminate of claim 2, wherein the basis weight of the nonelastic web is from about 1 ounce per square yard to about 5 ounces per square yard.

5. The laminate of claim 2, wherein said polyetherurethane material has a melt flow of from about 30 grams per 10 minutes to about 60 grams per 10 minutes when measured at 190 degrees C. under a 8,700 gram load.

6. The laminate of claim 2, wherein said meltblown fibers are meltblown microfibers.

7. The laminate of claim 2, wherein the nonelastic web is apertured.

8. The laminate of claim 2, wherein the nonelastic web further comprises fibers selected from the group consisting of rayon fibers or wood pulp fibers.

9. The laminate of claim 2, further comprising a dry laid nonelastic nonwoven web comprising from about 78 percent, by weight, to about 82 percent, by weight, of polyester staple fibers and from about 18 percent, by weight, to about 22 percent, by weight, of a polyester-based hot melt adhesive with said dry laid web being joined to said elastic sheet at least at two areas and with said dry laid web being gathered between said two areas.

10. An elastic stretch-bonded laminate adapted to stretch at least about 50 percent in at least one direction, said laminate comprising:
    an elastic nonwoven web, said elastic web comprising fibers of a polyetherurethane material; and
    at least one nonelastic nonwoven web of spunlaced hydraulically entangled polyester fibers joined to said elastic web at least at two areas, said nonelastic web being gathered between said two areas.

11. The stretch-bonded laminate of claim 10, wherein said polyetherurethane fibers are meltblown fibers.

12. The stretch-bonded laminate of claim 11, wherein the basis weight of the elastic nonwoven web is from about 10 grams per square meter to about 200 grams per square meter.

13. The stretch-bonded laminate of claim 11, wherein the basis weight of the nonelastic web is from about 1 ounce per square yard to about 5 ounces per square yard.

14. The stretch-bonded laminate of claim 11, wherein said polyetherurethane material has a melt flow of from about 30 grams per 10 minutes to about 60 grams per 10 minutes when measured at 190 degrees C. under a 8,700 gram load.

15. The stretch-bonded laminate of claim 11, wherein said meltblown fibers are meltblown microfibers.

16. The stretch-bonded laminate of claim 11, wherein the nonelastic web is apertured.

17. The stretch-bonded laminate of claim 11, wherein the nonelastic web further comprises fibers selected from the group consisting of rayon fibers or wood pulp fibers.

18. The stretch-bonded laminate of claim 11, further comprising a dry laid nonelastic nonwoven web comprising from about 78 percent, by weight, to about 82 percent, by weight, of polyester staple fibers and from about 18 percent, by weight, to about 22 percent, by weight, of a polyester-based hot melt adhesive with said dry laid web being joined to said elastic sheet at least at two areas and with said dry laid web being gathered between said two areas.

19. An elastic palindromic stretch-bonded laminate adapted to stretch at least about 75 percent in at least one direction, said laminate comprising:
    an inner elastic nonwoven web having a basis weight of from about 20 grams per square meter to about 100 grams per square meter, said elastic web comprising meltblown fibers of a polyetherurethane material having a melt index of from about 5 grams per 10 minutes to about 20 grams per 10 minutes when measured at 190 degrees C. under a 2,160 gram load; and two outer nonelastic nonwoven webs comprising spunlaced hydraulically entangled polyester fibers, said nonelastic webs each having a basis weight of from about 1 ounce per square yard to about 5 ounces per square yard.

20. The palindromic stretch-bonded laminate of claim 19, wherein the nonelastic web further comprises fibers selected from the group consisting of rayon fibers or wood pulp fibers.

21. The palindromic stretch-bonded laminate of claim 19, wherein said meltblown fibers are meltblown microfibers.

22. The palindromic stretch-bonded laminate of claim 19, wherein the nonelastic web is apertured.

* * * * *

UNITED STATES PATENT AND TRADEMARK OFFICE
CERTIFICATE OF CORRECTION

PATENT NO. : 4,692,368
DATED : September 8, 1987
INVENTOR(S) : Jack D. Taylor and L. Warren Collier, IV It is certified that error appears in the above—identified patent and that said Letters Patent is hereby corrected as shown below:

Column 1, line 66, "(0.5 inch)" should read --(0.4 inch)--

Column 4, line 13, "weight if" should read --weight of--

Column 4, line 56, "1.1 ounches" should read --1.1 ounces--

Column 6, line 49, "1.0 ounches" should read --1.0 ounces--

Signed and Sealed this

Second Day of February, 1988

Attest:

DONALD J. QUIGG

Attesting Officer

Commissioner of Patents and Trademarks